(12) United States Patent
Nicholls (10) Patent No.: US 8,114,109 B2
(45) Date of Patent: Feb. 14, 2012

(54) SINGLE-USE SKIN PRICKING DEVICE

(75) Inventor: Clive Nicholls, Buckinghamshire (GB)

(73) Assignee: Owen Mumford Limited, Oxford (GB)

( * ) Notice: Subject to any disclaimer, the term of this patent is extended or adjusted under 35 U.S.C. 154(b) by 415 days.

(21) Appl. No.: 12/162,430

(22) PCT Filed: Jan. 11, 2007

(86) PCT No.: PCT/GB2007/050010
§ 371 (c)(1),
(2), (4) Date: Jul. 28, 2008

(87) PCT Pub. No.: WO2007/088394
PCT Pub. Date: Aug. 9, 2007

(65) Prior Publication Data
US 2009/0048621 A1 Feb. 19, 2009

(30) Foreign Application Priority Data

Jan. 31, 2006 (GB) .................................. 0601912.9

(51) Int. Cl.
*A61B 17/32* (2006.01)
(52) U.S. Cl. ........................ 606/182; 606/181
(58) Field of Classification Search ................. 606/182, 606/181, 185, 167, 183; 600/583, 573; 604/93.01, 604/110, 111, 117, 158, 164.01, 192, 272, 604/890.1, 198; 227/67
See application file for complete search history.

(56) References Cited

U.S. PATENT DOCUMENTS

| | | | |
|---|---|---|---|
| 5,423,847 A * | 6/1995 | Strong et al. | 606/182 |
| 5,755,733 A * | 5/1998 | Morita | 606/182 |
| 2003/0050656 A1 | 3/2003 | Schraga | |
| 2003/0153939 A1 * | 8/2003 | Fritz et al. | 606/181 |
| 2005/0085840 A1 * | 4/2005 | Yi et al. | 606/182 |
| 2006/0052809 A1 * | 3/2006 | Karbowniczek et al. | 606/181 |

FOREIGN PATENT DOCUMENTS

| | | |
|---|---|---|
| EP | 0 747 006 | 12/1996 |
| EP | 0975938 | 3/1998 |
| EP | 1204371 | 5/2002 |
| EP | 1204372 | 5/2002 |
| EP | 1 247 489 | 10/2002 |
| GB | 2421439 | 6/2006 |

(Continued)

OTHER PUBLICATIONS

International Search Report for corresponding Application No. PCT/GB2007/050010 mailed Apr. 18, 2007.

(Continued)

*Primary Examiner* — Ryan Severson
*Assistant Examiner* — Tin Nguyen
(74) *Attorney, Agent, or Firm* — Young & Thompson (57) ABSTRACT

A single-use skin pricking device (7) comprising a housing (8), a lancet (1) disposed (5) within the housing (8), biasing means (11) coupled between the housing (8) and the lancet (1), and a trigger (12) mounted to the housing (8) for relative movement therewith. The trigger (8) is releasably coupled to the lancet (1) such that movement of the trigger (8) in a first direction moves the lancet (1) in a direction to compress the biasing means (11), and then causes release of the lancet (1) from (10) the trigger (8) whereby the biasing means (11) drives the lancet (1) in a second direction substantially opposite to said first direction.

14 Claims, 6 Drawing Sheets

FOREIGN PATENT DOCUMENTS

| | | |
|---|---|---|
| WO | 93/09723 | 5/1993 |
| WO | 00/78203 | 12/2000 |
| WO | 01/13794 | 3/2001 |
| WO | 03/071940 | 9/2003 |
| WO | 2006/067119 | 6/2006 |

OTHER PUBLICATIONS

British Search Report for corresponding Application No. GB0601912.9 dated Sep. 20, 2006.

* cited by examiner

SINGLE-USE SKIN PRICKING DEVICE

The present invention relates to single-use skin pricking devices.

Skin pricking devices are well known in the art. Typically, skin pricking devices have a lancet comprising a needle having a sharp tip at one end and being embedded in a plastics body at the opposite end, with the tip of the needle protruding from the body. Often the tip is enclosed within a cap to prevent accidental finger pricking and to maintain sterility of the needle, and the cap is removed before use of the lancet. Such lancets are used to obtain a small blood sample for analysis. Many single-use skin pricking devices have been devised to make the procedure of skin pricking as simple and safe as possible. Such single-use skin pricking devices typically include a holder for holding the lancet body, and a firing mechanism. The firing mechanism is configured to push the needle of the lancet into the skin for a predetermined distance or using a predetermined force. An example of such a firing device is described in EP1204371.

Known skin pricking devices typically require that the user performs several operations in order to safely fire the device. These include removing packaging from the device, removing the safety cap from the device, and pressing a trigger to fire the device. Some skin pricking devices also require cocking the lancet before firing, and some require recapping of the needle after firing, although most retract the needle into the device to avoid accidental skin pricking.

This number of steps is inconvenient and requires the user to use both hands when removing or replacing a cap, or removing packaging. It is realised that a device that requires fewer steps to fire would be more convenient to use, and furthermore a device that can be fired using only one hand would be advantageous, especially to users who may have limited use of their hands.

According to a first aspect of the invention there is provided a single-use skin pricking device comprising:
a housing;
a lancet disposed within the housing;
biasing means coupled between the housing and the lancet;
a trigger mounted to the housing for relative movement therewith, the trigger being releasably coupled to the lancet such that movement of the trigger in a first direction moves the lancet in a direction to compress the biasing means, and then causes release of the lancet from the trigger whereby the biasing means drives the lancet in a second direction substantially opposite to the first direction.

Preferably, the lancet comprises a cap covering an end of a needle, wherein the movement of the trigger in the first direction first causes the cap to be removed from the lancet to expose the needle. The cap is preferably substantially fixed relative to the housing.

It is preferred that the device comprises one or more guide tracks disposed within the housing for guiding movement of the lancet within the housing. The guide track may be substantially U-shaped.

It is preferred that the trigger is coupled to the lancet by slip means, the slip means allowing the trigger to disengage from the lancet at some predefined point of travel in the first direction. In one embodiment of the invention, the slip means comprises trigger wedges formed on the trigger and wedge engaging formations formed on the lancet, the trigger wedges engaging the formations as the trigger moves in the first direction up to a point of travel where the lancet moves to disengage the wedges from the formations to release the lancet.

Preferably, the biasing means is arranged to retract the lancet fully within the housing once the device has been fired. The biasing means may be formed integrally with the housing. In one embodiment of the present invention, the biasing means is partially preloaded prior to depressing the trigger.

It is preferred that the biasing means comprises a helical spring.

Preferably, the trigger comprises an opening through a lancet needle projects when the device is fired. It is also preferred that the trigger is actuated by pressing it directly against an area of skin to be pricked.

In one embodiment of the invention, the trigger and the housing may be moulded integrally with a weakened portion disposed at an interface between the trigger and the housing, the weakened portion configured to be broken when the trigger is pressed.

The device preferably comprises a locking mechanism arranged to lock the trigger relative to the housing in a predetermined position once the trigger has been pressed.

The device may also comprise a window provided in the housing to allow a user to view the lancet.

According to a second aspect of the invention, there is provided a single-use skin pricking device comprising:
a housing;
a lancet disposed within the housing;
a spring coupled between the housing and the lancet;
a guide track within the housing, the lancet being mounted in the guide track; and
a trigger releasably coupled to the lancet and having an opening formed therein through which a needle of the lancet can project.

Preferably, the track is substantially U-shaped.

It is preferred that the trigger is telescopically mounted in the housing.

Preferably, the legs of the U-shaped track lie substantially parallel to the direction of movement of the trigger.

An advantage of this single use skin pricking device is that the device can be operated with one hand, and that a single movement of the trigger effects uncapping the lancet, moving the lancet into a cocked position and firing the lancet.

For a better understanding of the present invention and in order to show how the same may be carried into effect reference will now be made by way of example to the accompanying drawings in which.

Figure 1:
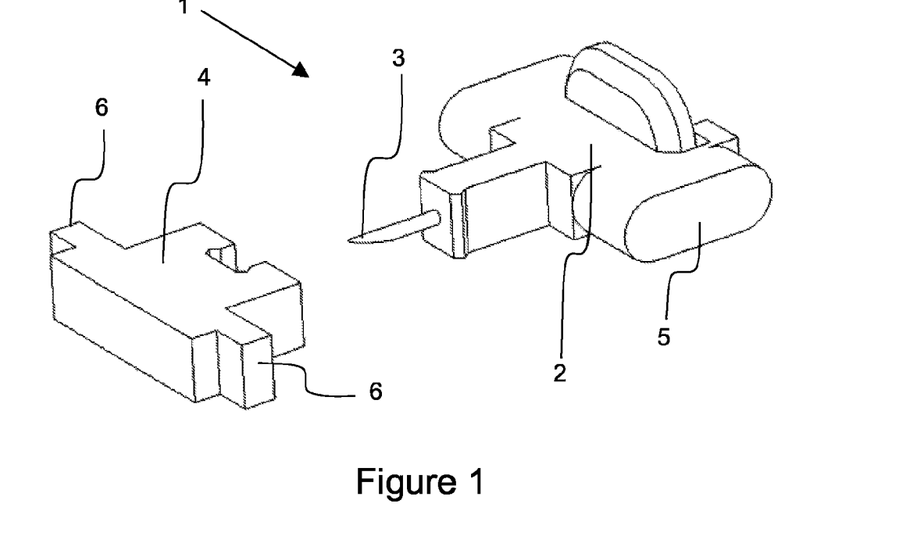
FIG. 1 is a perspective view of a lancet for use in a single-use skin pricking device.

Referring to FIG. 1, a lancet 1 comprises a moulded plastics lancet body 2 with a needle 3 partially embedded in the lancet body 2. A tip of the needle 3 projects from the lancet body 2. A cap 4 covers the tip of the needle 3 to maintain sterility prior to use. The cap 4 may be over-moulded onto the needle tip provided that the needle 3 is embedded more firmly in the body 2 than the cap 4.

The lancet body further comprises a pair of shaped guide portions 5 extending either side of the lancet body. The lancet cap 4 comprises a pair of fixing projections 6 disposed either side of the lancet cap 4.

Figure 2:
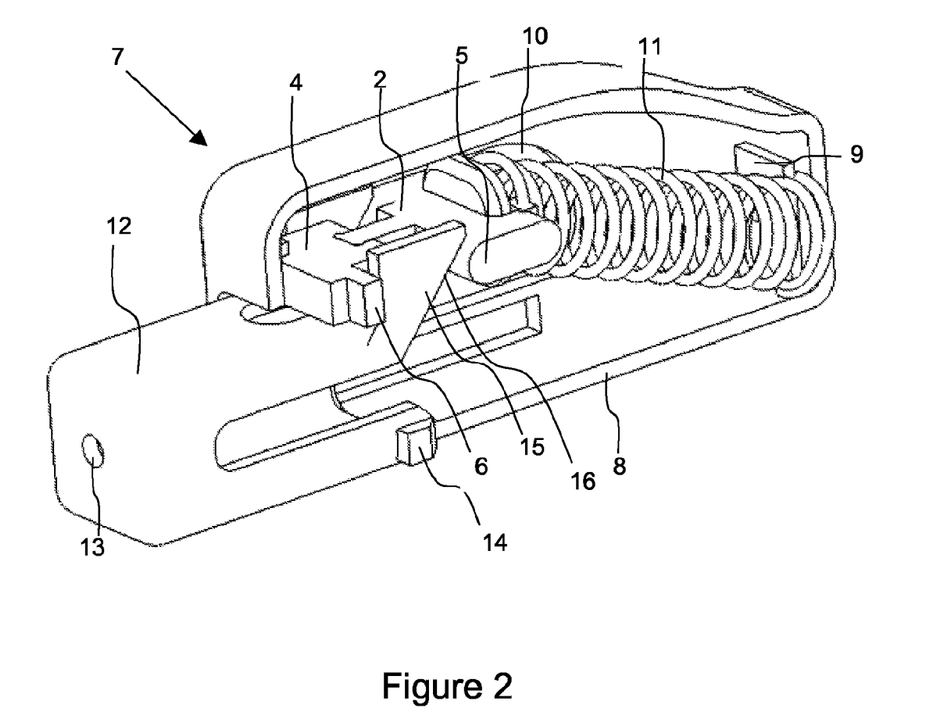
FIG. 2 is a perspective view of a single-use skin-pricking device with one side of a housing removed.

The single-use skin pricking device 7 comprises a housing 8. The housing is moulded as two separate symmetrical halves that may be pressed, snapped, welded or glued together to form the complete housing 8. FIG. 2 shows one half of the housing removed to show the interior cavity formed by the housing 8. Each half of the housing 8 comprises a spring holder 9 disposed at a rearward portion of the housing 8, and each half further comprises a lancet body guide track 10 moulded on the housing 8. The guide track 10 follows a substantially 'U'-shaped path along the inner surface of the housing 8, with the bight of the 'U' disposed towards the spring holder 9.

A spring 11 is disposed within the interior of the housing 8, and is held at one end of the spring 11 by the spring holder 9, and at the other end to the lancet body 2. The spring 11 is made of any suitable material such as metal or plastics. In particular, where the spring 11 is made of a plastics material, it may be integrally moulded as part of the housing 8. However, it is preferred to use a metal helical spring.

Once inserted, the lancet body 2 and the lancet cap 4 are both disposed within the housing 8. The lancet body guide portions 5 are configured to cooperate on each side with the lancet body guide track 10. The lancet cap fixing projections 6 are held in place by the housing 8 such that the lancet cap 4 does not move relative to the housing 8 following assembly. Alternatively, the lancet cap 4 may be moulded integrally with the housing 8, although this is not preferred as the lancet cap 4 must be sterile, and moulding the lancet cap 4 integrally with the housing 8 necessitates the manufacturing and assembly process to be carried out in a sterile environment.

Figure 3:
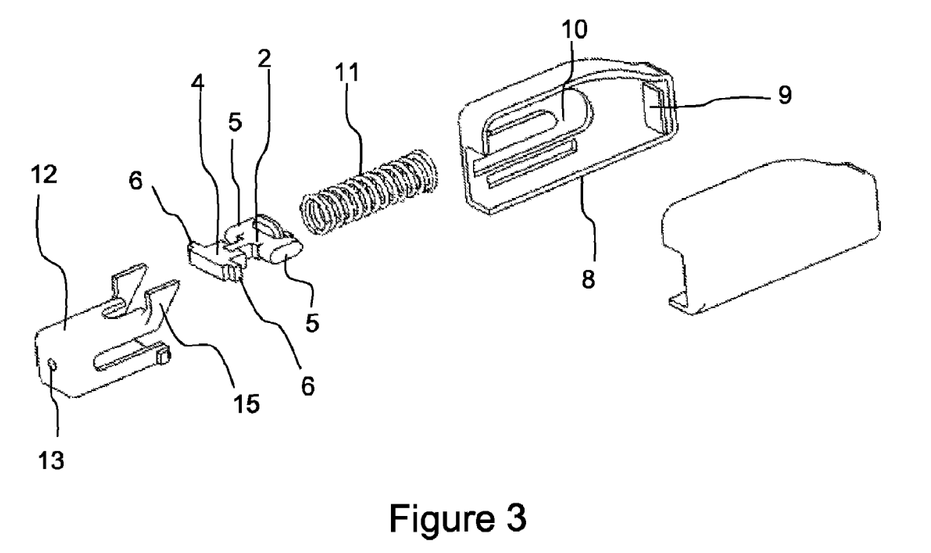
FIG. 3 is an exploded perspective view of the single-use skin pricking device of FIG. 2.
Figure 4:
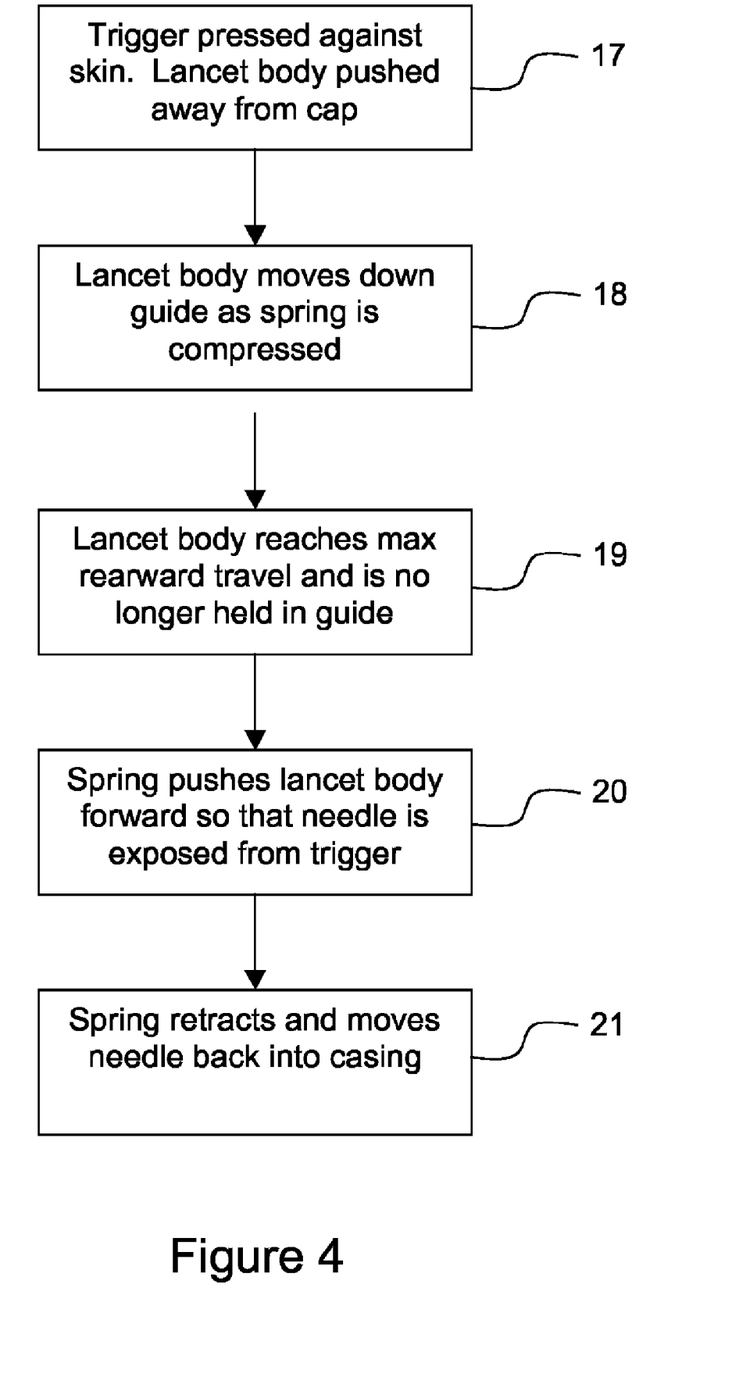
FIG. 4 is a flow diagram illustrating the stages in using the single-use skin pricking device.

The single-use skin pricking device further comprises a trigger 12. The trigger 12 is connected to the housing 8 and can telescope into an opening in the housing 8 when pressure is applied to the trigger 12. The trigger 10 comprises an opening 13 through which the lancet needle 3 can project. The trigger 12 further comprises guide lugs 14 to cooperate with the housing 8 and ensure that the trigger moves linearly along the main axis of the single-use skin pricking device 7 relative to the housing 8. The trigger 12 further comprises a pair of trigger wedges 15. The trigger wedges 15 each have an angled surface 16 with respect to a longitudinal axis of the single-use skin pricking device 7. The angled surfaces 16 are configured, in use, to contact the guide portions 5 of the lancet body 2.

The trigger 12 may be moulded separately from the housing 8, or may be moulded integrally with the housing 8 with a weakened area connecting the housing 8 and the trigger 12 to allow the trigger to "break free" of the housing 8 to allow movement of the trigger 12 relative to the housing 8.

Figure 5:
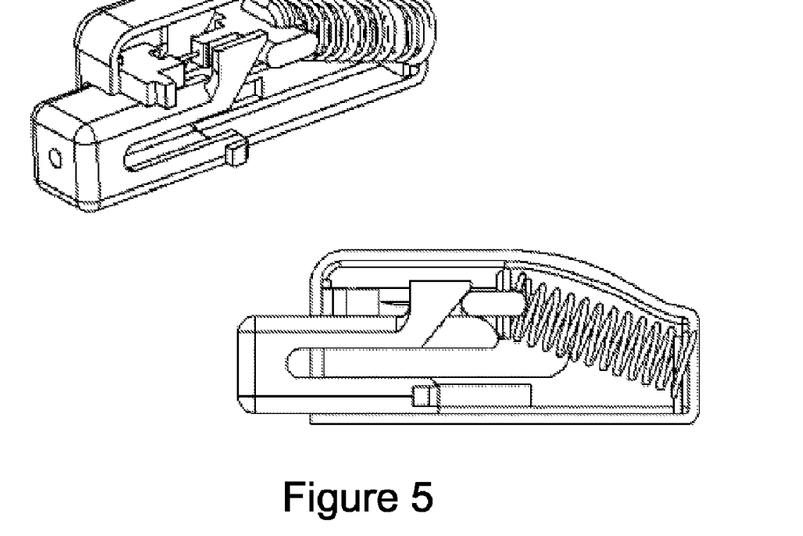
FIG. 5 is a perspective view and a side elevation view of the single-use skin pricking device with one side of the housing removed with a trigger partially depressed.

When a user receives the single-use skin pricking device 7, it is in the configuration shown in FIG. 2, with the trigger 12 extending from the housing 8 and the lancet cap 4 in place over the lancet needle 3. To fire the device, the user presses the trigger 12 against the skin. The steps illustrated in FIG. 3 are then followed. When the trigger is pressed against the skin (step 17), the angled surfaces 16 of the trigger wedges 15 contact the guide portions 5 of the lancet body 2. This pushes the lancet body 2 away from the lancet cap 4, thereby removing the cap 4 from the lancet needle 3, as illustrated in FIG. 5.

Figure 6:
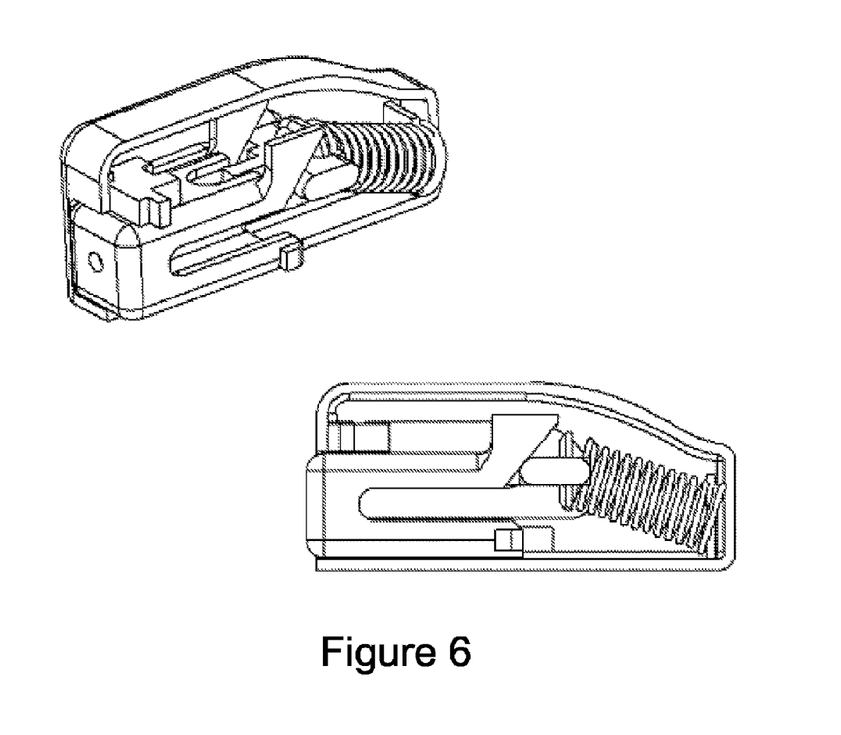
FIG. 6 is a perspective view and a side elevation view of the single-use skin pricking device with one side of the housing removed with the trigger further depressed.

As the trigger 12 is further pressed, it moves into the interior of the housing 8, as shown in FIG. 6. The spring 11 compresses (step 18) and the angled surfaces 16 of the trigger projections 15 push the lancet body 4 further away from the cap 4. Owing to the cooperation between the each guide portion 5 of the lancet body 2 and the guide track 10, the lancet body 6 moves in a first direction down one leg of the 'U' towards the spring holder 9 at the rear of the housing 8. As the trigger wedges 15 comprise angled surfaces 16, the lancet body 2 slips down the angled surfaces 16 as the body 2 is pushed by the trigger 12.

Figure 7:
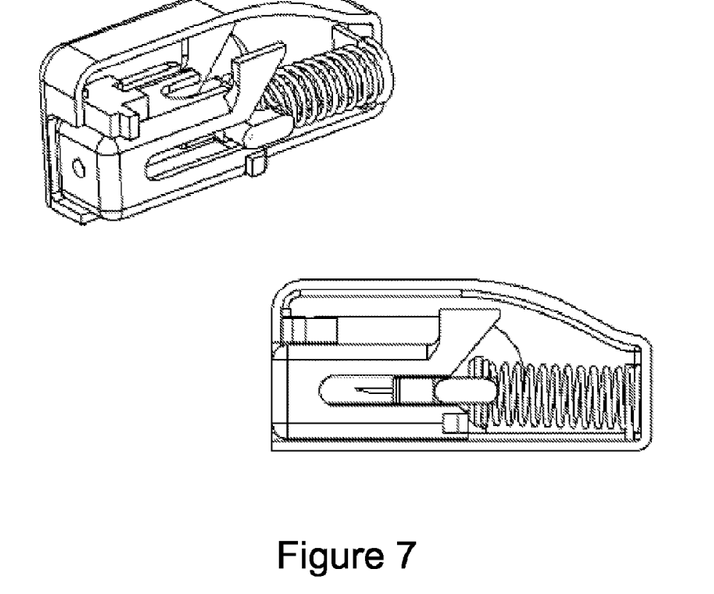
FIG. 7 is a perspective view and a side elevation view of the single-use skin pricking device with one side of the housing removed with the trigger fully depressed.

Once the lancet body 4 has reached its rearward maximum travel (step 19) in the housing 8, it has reached the apex of the U-shaped guide tracks 10 and can no longer move back towards the cap 4. The angled surfaces 16 of the trigger wedges 15 cause the guide portions 5 of the lancet body 2 to slip entirely away from the trigger wedges 15 such the lancet body 2 is no longer held by the trigger wedges 15. At this point, the spring 11 is at maximum compression and the trigger 12 is fully retracted into the housing 8.

Figure 8:
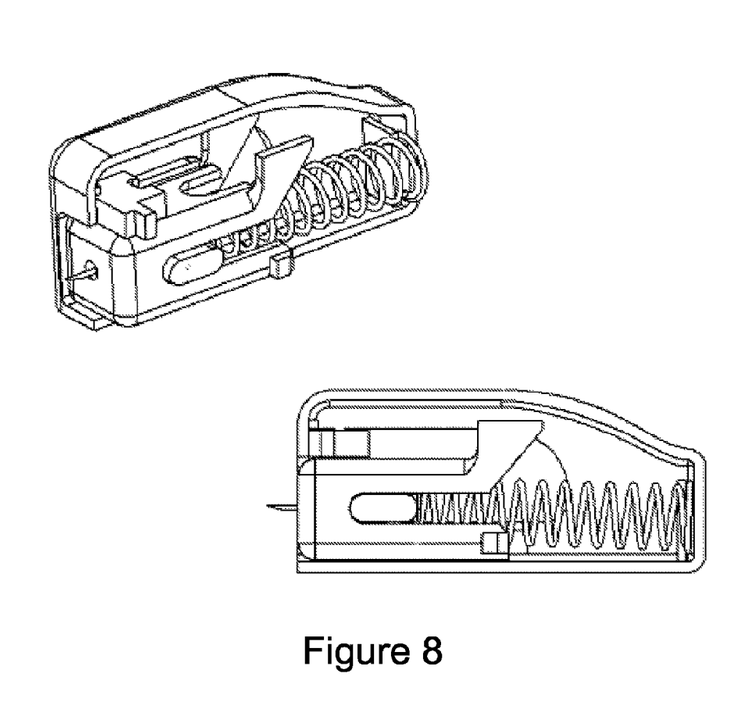
FIG. 8 is a perspective view and a side elevation view of the single-use skin pricking device with one side of a housing removed with the trigger fully depressed and the lancet needle exposed from the single-use skin pricking device.

The spring 11 pushes the lancet body 2 down over the guide portions 5 until the body 2 is free of the wedges 15. The lancet body 4 is then fired forward (step 20) by the rapid expansion of the spring 11. The lancet body 4 is pushed in a second direction determined by a co-operation between each lancet guide portion 5 and the lower legs of the guide track 10. The lancet body 4 moves such that the needle tip 3 of the lancet projects from the opening 13 in the trigger 12 and pricks the skin. The lancet body 4 contacts the front face of the trigger 12. This limits the distance that the needle 3 can protrude from the opening 133, thereby preventing the needle 3 from penetrating the skin too deeply.

Figure 9:
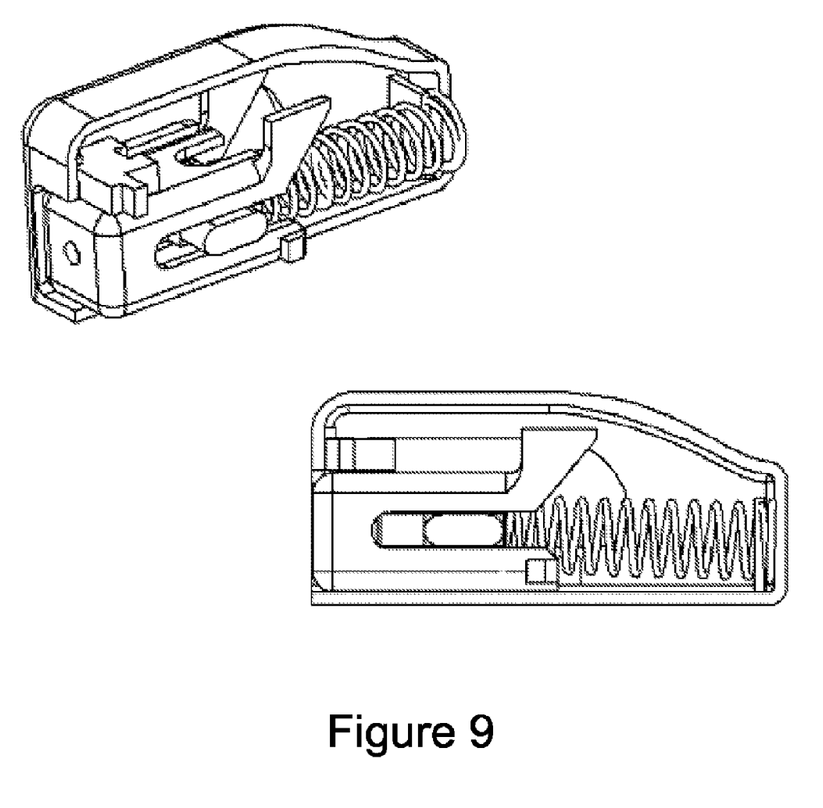
FIG. 9 is a perspective view and a side elevation view of the single-use skin pricking device with one side of the housing removed with the trigger fully depressed and the lancet needle retracted into the single-use skin pricking device.

At this point the spring 11 is overextended, so the spring 11 retracts (step 21) to pull the needle 3 back through the opening 13, thereby holding the needle 3 within the interior of the single-use skin pricking device 7 to prevent any skin pricking accidents being caused by the needle 20. Once the single-use skin pricking device 7 has been used, it cannot be reset without completely disassembling the device.

A clip or lock may be provided to lock the trigger 12 inside the housing 8 once the device has been fired to indicate to the user that the device has been used and should be disposed of.

As the needle 3 is sterile when it is embedded in the cap 4, and does not contact any other part of the single-use skin pricking device 7 before it pricks the skin, there is no need to sterilize or seal the housing 8 or the parts contained within the housing 8, other than the needle 3 and the surrounding cap 4.

In order to ensure that the spring 11 fires the lancet with sufficient force to project from the opening 13 in the trigger 12, the spring 11 may be partially pre-loaded prior to assembly of the device 7.

It will be appreciated by those of skill in the art that various modifications may be made to the above described embodiment without departing from the scope of the present invention. For example, a window may be provided in the wall of the housing 8 to allow the user to observe the lancet contained within the housing prior to use. This is enables the user to ensure that the cap 4 and lancet body 2 have not been separated prior to use.

The invention claimed is:

1. A single-use skin pricking device comprising:
a housing defining an opening at one end;
a lancet disposed within the housing, the lancet comprising a cap covering an end of a needle;
biasing means coupled between the housing and the lancet;
a trigger mounted telescopically within said opening of the housing for relative movement therewith, the trigger being releasably coupled to the lancet such that movement of the trigger in a first direction into an interior of the housing moves the lancet along a U-shaped guide track along an inner surface of the housing for guiding movement of the lancet in a direction to compress said biasing means, causes the cap to be removed from the lancet to expose the needle, and then causes release of the lancet from the trigger whereby said biasing means drives the lancet in a second direction substantially opposite to said first direction.

2. The device according to claim 1, wherein said cap is substantially fixed relative to said housing.

3. The device according to claim 1, wherein the trigger is coupled to the lancet by slip means, the slip means allowing the trigger to disengage from the lancet at some predefined point of travel in said first direction.

4. The device according to claim 3, said slip means comprising trigger wedges formed on the trigger and wedge engaging formations formed on the lancet, the trigger wedges engaging said formations as the trigger moves in said first direction up to a point of travel where the lancet moves to disengage the wedges from the formations to release the lancet.

5. The device according to claim 1, wherein the biasing means is arranged to retract the lancet fully within the housing once the device has been fired.

6. The device according to claim 1, wherein the biasing means is formed integrally with the housing.

7. The device according to claim 1, wherein the biasing means is partially preloaded prior to depressing the trigger.

8. The device according to claim 1, wherein the biasing means comprises a helical spring.

9. The device according to claim 1, wherein the trigger comprises an opening through a lancet needle projects when the device is fired.

10. The device according to claim 1, wherein the trigger is actuated by pressing it directly against an area of skin to be pricked.

11. The device according to claim 1, wherein the trigger and the housing are moulded integrally with a weakened portion disposed at an interface between the trigger and the housing, the weakened portion configured to be broken when the trigger is pressed.

12. The device according to claim 1, further comprising a locking mechanism arranged to lock the trigger relative to the housing in a predetermined position once the trigger has been pressed.

13. The device according to claim 1, further comprising a window provided in the housing to allow a user to view the lancet.

14. The device according to claim 1, wherein the cap comprises a pair of fixing projections disposed either side of the cap.

* * * * *